12/88 660 XR 4,718,421
128 660

United States Patent [19]

Rohwedder et al.

[11] Patent Number: 4,718,421

[45] Date of Patent: Jan. 12, 1988

[54] ULTRASOUND GENERATOR

[75] Inventors: Arnim Rohwedder; Gerd Wessels, both of Erlangen, Fed. Rep. of Germany

[73] Assignee: Siemens Aktiengesellschaft, Berlin and Munich, Fed. Rep. of Germany

[21] Appl. No.: 890,103

[22] Filed: Jul. 28, 1986

[30] Foreign Application Priority Data

Aug. 9, 1985 [DE] Fed. Rep. of Germany ....... 3528676

[51] Int. Cl.[4] ............................................. A61B 17/00

[52] U.S. Cl. .................................... 128/328; 128/660; 310/325; 310/326

[58] Field of Search ............... 128/330, 328, 652, 660, 128/639, 24 A, 343; 310/316, 317, 334, 323, 325, 326, 335; 73/606, 620, 633

[56] References Cited

U.S. PATENT DOCUMENTS

| | | | |
|---|---|---|---|
| 2,525,873 | 10/1950 | De Lano, Jr. . | |
| 2,592,222 | 4/1952 | Williams . | |
| 3,387,604 | 6/1968 | Erikson . | |
| 4,084,582 | 4/1978 | Nigam | 128/660 |
| 4,340,944 | 7/1982 | Dory . | |
| 4,588,917 | 5/1986 | Ratcliff | 310/317 |

FOREIGN PATENT DOCUMENTS

| | | |
|---|---|---|
| 0018614 | 11/1980 | European Pat. Off. . |
| 0036353 | 9/1981 | European Pat. Off. . |
| 0118837 | 9/1984 | European Pat. Off. . |
| 3319871 | 12/1984 | Fed. Rep. of Germany . |
| 1593791 | 7/1970 | France . |
| 2140693 | 12/1984 | United Kingdom . |

OTHER PUBLICATIONS

Ultrasonic Transceiver, vol. 9, No. 150 (E-324) (1873) Jun. 25, 1985; Yokokawa Hokushin Denki K.K.

*Primary Examiner*—C. Fred Rosenbaum
*Assistant Examiner*—Gene B. Kartchner
*Attorney, Agent, or Firm*—Hill, Van Santen, Steadman & Simpson

[57] ABSTRACT

An ultrasound generator for acoustic irradiation of pathological changes of a human body comprises a planarly fashioned piezo-electric transducer which is acoustically coupled to an acoustical lens on one surface by a soft metal layer and is acoustically coupled on the opposite surface by a second soft metal layer to a dampening member. The soft metal layers act as both acoustically coupling layers and as electrodes for the piezo-electric transducer. The piezo-electric transducer can be formed of either a plurality of layers which are spaced apart by soft metal layers acting as electrodes, a single piezo-electric plate, or a plurality of plates arranged side by side in the same plane.

20 Claims, 2 Drawing Figures

ULTRASOUND GENERATOR

BACKGROUND OF THE INVENTION

The invention is directed to an ultrasound generator for the acoustic irradiation of pathological changes in a human body. The generator comprises a planarly fashioned piezoelectric transducer which is provided with electrodes on both its front and back surfaces, is acoustically coupled to an acoutical lens on the front surface or side and is also acoustically coupled to a dampening member on the back side or surface.

An ultrasound generator can service, for example, for generating shock waves for noncontacting disintegration of concrements or for the acoustic irradiation of pathological changed tissues in a human's body. U.S. Pat. No. 3,387,604 discloses an ultrasound generator wherein a lens is acoustically coupled to a front surface of a piezo-electric transducer by means of a casting process and a dampening member is acoustically coupled to the back surface of the piezo-electric transducer by glue. The front surface and back surface of the piezo-electric transducer also are provided with electrodes which are a conductive coating, for example a silver lacquer. Since the transducer must first be provided with electrodes and then measures for the acoustic coupling of a lens and the dampening material must be undertaken subsequent to this, the known ultrasound generator can, thus, only be manufactured in an involved way.

SUMMARY OF THE INVENTION

The object of the present invention is to provide an ultrasound generator having an acoustical lens and a dampening member of a structure wherein the piezo-electric transducer can be equipped with electrodes in a simple way and the piezo-electric transducer can be acoustically coupled to the lens and the dampening member in a very simple way.

This object is achieved in accordance with the present invention by an improvement in an ultrasound generator for an acoustic irradiation of pathological changes in a human body, said generator comprising a planarly fashioned piezo-electric transducer which is acoustically coupled on a first or a front surface to the acoustical lens and is acoustically coupled on a second or back surface to a dampening member, said transducer is provided with electrodes on both the front and back surface. The improvements are that layers of a soft metal are provided between the piezo-electric transducer and both the acoustical lens and the dampening member and that these layers simultaneously serve both as electrodes and for acoustically coupling the piezo-electric transducer to the respective lens and dampening member. Thus, in order to provide the piezo-electric transducer with both electrodes and in order to acoustically couple it to the lens and dampening member, the only thing required is the application of the thin plates of soft metal, for example lead, to the front surface and to the back surface of the piezo-electric transducer and to keep these pressed in between the piezo-electric transducer and the acoustical lens as well as the dampening member.

Given the ultrasound generator of the invention, the piezo-electric transducer can be fashioned in an extremely simple way in that, for example, is manufactured as a single plate of piezo-electric material. Even in the case where a plurality of plates of piezo-electric material are arranged in one plane to construct the piezo-electric transducer, a simplification over the prior art occurs because all the plates are contacted in an extremely simple way by means of the layers of soft metal and are coupled to the lens and to the dampening member in an extremely simple fashion. Every plate can thereby be formed of a single layer of piezo-electric material but can also be formed of a plurality of layers of piezo-electric material superimposed on one another with a soft metal layer being arranged between each of the piezo-electric layers and forming the individual contact electrodes. Thus, an extremely simple contacting and coupling of the transducer to both the lens and the dampening means will occur in comparison to the prior art. Moreover, an efficient acoustical coupling of the layer of the piezo-electric material to one another is also established.

The acoustical lens can advantageously be composed of a material whose sound impedance is greater than or equal to the geometric mean of the sound impedances of the material of the piezo-electric transducer and of water. It being assumed that the acoustical impedance of water essentially corresponds to that of the tissue to be acoustically irradiated.

The acoustical lens are composed of two parts of which the first part comprises a fixed focus member with an emission surface and is acoustically coupled to the piezo-electric transducer. The second part comprises of variable focused member which is acoustically coupled to the emission surface of the first part. A focus displacement and, thus, an optimum adaptation of the position of the focus to the respective conditions, for example, an adjustment to a renal calculus, is possible on the basis of this construction. The first part is thereby expediently constructed of a material having a lower acoustical impedance than the piezo-electric transducer, for example, a light metal selected from a group consisting of magnesium, aluminum, a magnesium alloy or an aluminum alloy. The second part can be formed by a liquid lens, which is integrated into the first part and which is adapted in shape to the respectively desired focus position on the basis of the liquid pressure. However, instead of the liquid lens, a solid state lens can also be employed. The focus displacement can also occur by dislocation of the solid state lens or by a temperature modification.

DESCRIPTION OF THE PREFERRED EMBODIMENTS

Figure 1:
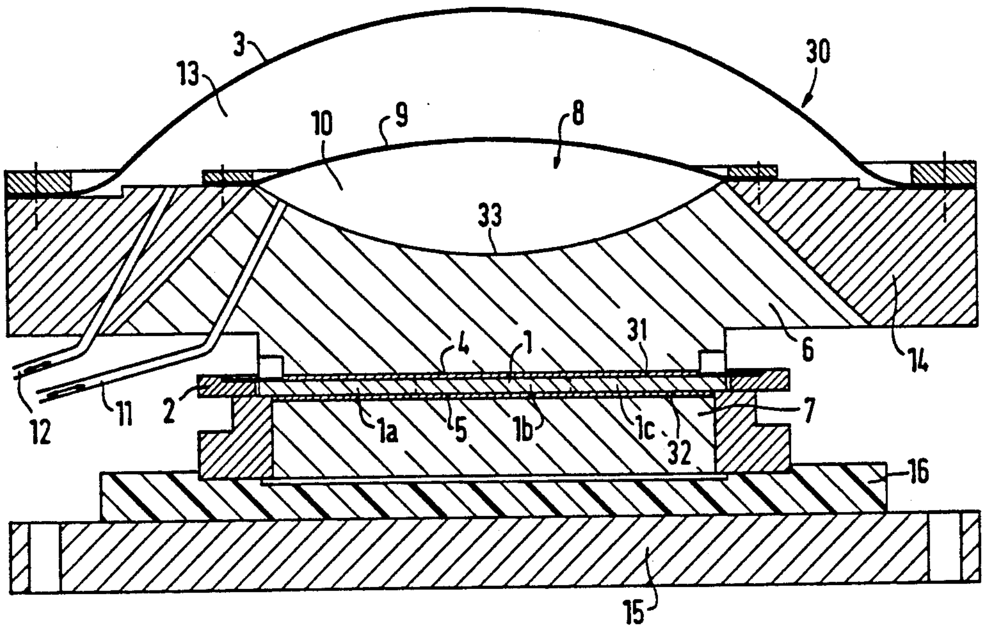
FIG. 1 is a cross sectional view through an ultrasound generator in accordance with the present invention.

The principles of the present invention are particularly useful in an ultrasound generator illustrated in FIG. 1 and generally indicated at 30. The generator 30 includes a piezo-electric transducer 1 forming a single transducer in the form of a planar plate which is secured in a ring 2 such as by glue. An electric contacting of the piezo-electric transducer 1 occurs by means of two lead plates 4 and 5. The plate 4 is pressed in between a front or top surface 31 of the piezo-electric transducer 1 and a first part 6 of an acoustical lens whereas the plate 5 is held between a back or bottom surface 32 of the piezo-electric transducer 1 and an acoustical dampening member 7. As a result of the lead plates 4 and 5, the acoustical coupling of the first part 6 of the acoustical lens and of the dampening member 7 to the piezo-electric transducer is guaranteed at the same time.

The first part 6 of the acoustical lens is held in a steel ring 14 and has a concave emission surface 33 which faces away from the transducer 1. The acoustical lens comprises a liquid lens 8 which is integrated into the part 6 which, for example, can be composed of magnesium by contacting the emission surface 33. The liquid lens 8 is formed by a membrane 9 which is stretched over the emission surface 33 and holds an acoustically favorable liquid 10. The acoustical lens then comprises the acoustical impedance which is greater than or equal to the geometric means of the acoustical impedance of the material of the piezo-electric transducer 1 and of water. The volume of the liquid lens 8 can be changes by a line 11 so that the shape of the liquid lens 8 is thereby changed and the resulting focus can be set in accordance with the respective requirements. The coupling of the ultrasound generator to the body to be treated can occur, for example, by an additional membrane 3 and the space between the membranes 9 and 3 is filled with a coupling agent 13, for example, water which can be introduced from a channel or line 12. The components 6, 9 and 11 are held by the steel ring 14.

A steel plate 15 serves as a reciprocal plate or base plate. An insulator plate 16 is arranged between the acoustical dampening member 7 and the steel plate 15.

As already initially mentioned, a single, planar plate as a piezo-electric transducer can also be replaced by a plurality of such plates of piezo-electric material arranged in a single plane. Thus, the plate 1 can be replaced by three plates 1*a*, 1*b* and 1*c*, which are placed side by side, as illustrated by the broken line in FIG. 1. The lead plates 4 and 5 thereby cover all of the plates 1*a*, 1*b* and 1*c*.

Figure 2:
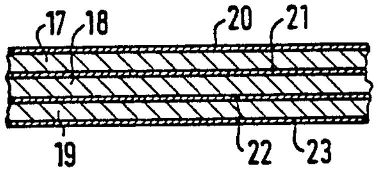
FIG. 2 is a cross sectional view of a modification of a piezo-electric transducer of the ultrasound generator of FIG. 1 and according to the invention.

In the example illustrated in FIG. 2, the piezo-electric transducer is formed by a plurality of layers 17, 18 and 19 of piezo-electric material which are covered by lead layers 20, 21, 22 and 23 which serve as the electrodes and for acoustical coupling. As illustrated, the lead layers 21 and 22 are sandwiched between the piezo-electric layers 17 and 18 and, 18 and 19 respectively while the lead layers 20 and 23 act as the outer layers.

The thickness on the order of magnitude greater than 1 mm and diamters greater than 10 mm comes into consideration for the piezo-electric transducer 1 for applications as a high intensity ultrasound generator for the acoustical irradiation of pathological changes. What is crucial is that the diameter of the transducer be greater than the thickness. Lead-zirconatetitanate can be utilized as the piezo-electric material.

In order to achieve different spectral components of the acoutical wave, a plurality of ceramics having different thicknesses can be arranged one above another and/or annularly relative to each other.

Although various minor modifications may be suggested by those versed in the art, it should be understood that we wish to embody with the scope of the patent granted hereon, all such modifications as reasonably and properly come within the scope of our contribution to the art.

We claim:

1. In an ultrasound generator for an acoustical irradiation of pathological changes in a human body, said generator comprising a planarly fashioned piezo-electric transducer which is acoustically coupled to an acoustical lens on a first surface and is acoustically coupled to a dampening member on a second surface opposite the first surface, said transducer being provided with electrodes on these two surfaces, the improvements comprising a layer of soft metal being provided adjacent each of the first and second surfaces and extending between the piezo-electric transducer and the acoustical lens as well as between the transducer and the dampening material, said layers of soft metal simultaneously serving as both electrodes for the transducer and for acoustically coupling the piezo-electric transducer respectively to the acoustical lens and the dampening member.

2. In an ultrasound generator according to claim 1, wherein the acoustical lens is composed of a material whose acoustical impedance is greater than or equal to the geometric means of the acoustical impedance of the material of the piezo-electric transducer and of water.

3. In an ultrasound generator according to claim 1, wherein the piezo-electric transducer is formed by a single plate of piezo-electric material.

4. In an ultrasound generator according to claim 1, wherein the piezo-electric transducer is formed by a plurality of plates of piezo-electric material arranged in one plane with the two layers of soft metal covering the plurality of plates on the first and second surfaces of the transducer to form the electrodes therefor.

5. In an ultrasound generator according to claim 4, wherein each of the piezo-electric plates is formed by a plurality of piezo-electric layers superimposed with a soft metal layer therebetween to act as individual electrodes for the superimposed layers.

6. In an ultrasound generator according to claim 1, wherein the piezo-electric transducer is formed by a plurality of superimposed layer of piezo-electric material, said layers being separated from one another by a layer of soft metal forming an individual electrode for the adjacent piezo-electric layers.

7. In an ultrasound generator for an acoustical irradiation of pathological changes in a human body, said generator comprising a planarly fashioned piezo-electric transducer which is acoustically coupled to an acoustical lens on a first surface and is acoustically coupled to a dampening member on a second surface opposite the first surface, said transducer being provided with electrodes on these two surfaces, the improvements comprising the acoustical lens being composed of two parts, the first of the two parts comprising a fixed focused member which is acoustically coupled directly to the piezo-electric transducer and the second of the two parts comprising a variable focused member and being acoustically coupled to an emission face of the first part, and a layer of soft metal being provided adjacent each of the first and second surfaces and extending between the piezo-electric transducer and the first part of the acoustical lens as well as between the transducer and the dampening material, said layers of soft metal simultaneously serving as both electrodes for the transducer and for acoustically coupling the piezo-electric transducer respectively to the first part of the acoustical lens and the dampening member.

8. In an ultrasound generator according to claim 7, wherein the first part is composed of light metal.

9. In an ultrasound generator according to claim 8, wherein said metal is selected from a group consisting of magnesium and magnesium alloys.

10. In an ultrasound generator according to claim 8, wherein said light metal is selected from a group consisting of aluminum and aluminum alloys.

11. In an ultrasound generator according to claim 7, wherein the second part is formed by a liquid lens which is integrated into the first part.

12. In an ultrasound generator according to claim 11, wherein the second part is formed of a light metal.

13. In an ultrasound generator according to claim 12, wherein said light metal is selected from a group consisting of aluminum, magnesium, magnesium alloys and aluminum alloys.

14. In an ultrasound generator according to claim 7, wherein the piezo-electric transducer is formed by a single plate of the piezo-electric material.

15. In an ultrasound generator according to claim 7, wherein the piezo-electric transducer is formed of a plurality of plates of piezo-electric material arranged in one plane with the edges together to form a single layer transducer with the single layer transducer being interposed between the two layers of soft metal.

16. In an ultrasound generator according to claim 15, wherein each plate comprises a plurality of superimposed layers of piezo-electric material having a soft metal layer arranged between the layers of piezo-electric material forming electrodes.

17. In an ultrasound generator according to claim 7, wherein the piezo-electric transducer is formed by a plurality of superimposed layers of piezo-electric material with each of the layers of piezo electric material being separated from the other layer by a layer of soft metal forming an individual contact electrode.

18. In an ultrasound generator according to claim 7, wherein each of the soft metal layers is a lead layer.

19. In an ultrasound generator for an acoustical irradiation of pathological changes in a human body, said generator comprising a planarly fashioned piezo-electric transducer which is acoustically coupled to an acoustical lens on a first surface and is acoustically coupled to a dampening member on a second surface opposite the first surface, said transducer being provided with electrodes on these two surfaces, the improvements comprising a layer of soft metal being provided between the piezo-electric transducer the acoustical lens as well as between the transducer and the dampening material, said layers of soft metal being lead and simultaneously serving as both electrodes for the transducer and for acoustically coupling the piezo-electric tranducer respectively to the acoustical lens and the dampening member.

20. In an ultrasound generator according to claim 19, wherein the acoustical lens is composed of two parts, the first of the two parts comprises a fixed focused member which is acoustically coupled directly to the piezo-electric transducer and the second of the two parts comprises a variable focused member and is acoustically coupled to emission face of the first part, said parts of the acoustical lens being composed of a material whose acoustical impedance is greater than or equal to the geometric means of the acoustical impedance of the material of the piezo-electric transducer and of water.

* * * * *